United States Patent [19]
Morgan et al.

[11] Patent Number: 6,060,712
[45] Date of Patent: May 9, 2000

[54] SCANNING LINE SOURCE FOR GAMMA CAMERA

[75] Inventors: Hugh T. Morgan, Highland Heights; Gregory G. Cooley, Chardon; Bryce G. Thornton, Concord; Steven J. Plummer, Hudson, all of Ohio

[73] Assignee: Picker International, Inc., Cleveland, Ohio

[21] Appl. No.: 09/018,609

[22] Filed: Feb. 4, 1998

Related U.S. Application Data

[63] Continuation-in-part of application No. 08/654,542, May 29, 1996, Pat. No. 5,834,780.

[51] Int. Cl.$^7$ .................................................. G01T 1/166
[52] U.S. Cl. ................................. 250/363.04; 250/503.1
[58] Field of Search .................... 250/363.03, 363.04, 250/363.05, 363.07, 363.08, 363.1, 503.1

[56] References Cited

U.S. PATENT DOCUMENTS

| | | |
|---|---|---|
| 4,255,664 | 3/1981 | Rutt et al. . |
| 4,672,648 | 6/1987 | Mattson et al. . |
| 5,210,421 | 5/1993 | Gullberg et al. . |
| 5,479,021 | 12/1995 | Morgan et al. . |
| 5,552,606 | 9/1996 | Jones et al. . |
| 5,576,545 | 11/1996 | Stoub et al. . |

FOREIGN PATENT DOCUMENTS

| | | |
|---|---|---|
| 58-92974 | 6/1983 | Japan . |
| 61-235782 | 10/1985 | Japan . |

OTHER PUBLICATIONS

Larsson, et al.; "Simultaneous SPECT and CT with Shutter Controlled Radionuclide Sources and Parallel Collimator Geometry" IEEE Trans. Nuc. Sci.; vol. 40, No. 4, Aug. 1993, pp. 117–1122.

Tan, et al.; "A Scanning Line Source for Simultaneous Emission and Transmission Measurements in SPECT"; The Journal of Nuc. Med., vol. 34, No. 10, Oct. 1993, pp. 1752–1760.
ADAC Laboratories Advertisement; Date Unknown.
U.S. application Ser. No. 08/374,977; Plummer, et al.; filed Jan. 19 1995; "Emission/Transmission Device for Use With a Dual Head Nuclear Medicine Gamma Camera With the Transmission Source Located Behind the Collimator".
U.S. application Ser. No. 08/483,276; Morgan, et al.; filed Jun. 7 1995; "Gamma Camera Split Collimator Collimation Method and Apparatus".

*Primary Examiner*—Constantine Hannaher
*Assistant Examiner*—Albert Gagliarol
*Attorney, Agent, or Firm*—Timothy B. Gurin; John J. Fry; Eugene E. Clair

[57] ABSTRACT

A gamma camera system includes two or more radiation detector heads and which are mounted opposite each other to a gantry for rotation about a subject. A transmission radiation source assembly is mounted to the front face of at least one of the detectors and can be moved across the face of the detector. The source assembly includes a radiation attenuating housing, a leaded bronze source holder, and a radionuclide source. The radionuclide source is retained in a longitudinal groove disposed in the source holder. The source holder may be rotated into open, closed, and access positions. The transmission radiation emitted by the source assembly is directed across the examination region, attenuated by the subject, and detected by the opposed detector. The gamma camera system also includes a filter which selectively attenuates the transmission radiation to obtain a desired attenuation profile which prevents saturation of the opposed detector. The filter includes at least one layer of radiation attenuating material of uniform thickness but varying in width in a direction substantially parallel to a direction of motion of the source assembly. An image representation is reconstructed using the radiation emitted by the subject and corrected in accordance with the transmitted radiation data.

16 Claims, 8 Drawing Sheets

Fig. 9D'
RADIATION BEAM
COUNT PROFILE

Fig. 9E'
RADIATION BEAM
COUNT PROFILE

Fig. 9F'
RADIATION BEAM
COUNT PROFILE

SCANNING LINE SOURCE FOR GAMMA CAMERA

CROSS REFERENCE TO RELATED APPLICATION

This application is a continuation-in-part of U.S. patent application Ser. No. 08/654,542, now U.S. Pat. No. 5,834,780, filed on May 29, 1996.

BACKGROUND OF THE INVENTION

The present invention relates to the art of diagnostic imaging. It finds particular application in conjunction with single-photon emission computed tomography (SPECT) with single or multi-headed cameras and will be described with particular reference thereto. It is to be appreciated, however, that the invention will also find application in other nuclear medicine and transmission radiation diagnostic imagers.

Heretofore, single photon emission computed tomography has been used to study a radionuclide distribution in subjects. Typically, one or more radiopharmaceuticals are injected into a subject. The radiopharmaceuticals are commonly injected into the subject's blood stream for imaging the circulatory system or for imaging specific organs which absorb the injected radiopharmaceuticals. Gamma or scintillation camera heads are placed closely adjacent to a surface of the subject to monitor and record emitted radiation. In single photon-emission computed tomography, the head is rotated or indexed around the subject to monitor the emitted radiation from a plurality of directions. The monitored radiation data from the multiplicity of directions is reconstructed into a three dimensional image representation of the radiopharmaceutical distribution within the subject.

A drawback to the SPECT imaging technique is that the patient is not completely homogeneous in terms of radiation attenuation or scatter. Rather, the human patient includes many different tissue and bone types which absorb or scatter radiation from the radiopharmaceuticals to different degrees. The SPECT images can be made more accurate if they are corrected for the radiation lost to scattering or attenuation along each path through the human torso.

Accordingly, transmission radiation sources have been placed opposite the patient from a detector head. In three detector head systems, for example as disclosed in U.S. Pat. No. 5,479,021, which is commonly owned with the present application, the fan beam radiation source is mounted to the rotating gantry between two of the detectors and opposite the third. Such a mounting arrangement is of course not applicable to opposed, two detector head systems.

In single head systems, for example as disclosed in Tan, *A Scanning Line Source for Simultaneous Emission and Transmission Measurements in SPECT*, J. Nuclear Med., Vol. 34, No. 10, Pg. 1752 (October 1993) a scanning line source is mounted on a frame attached to the collimator of the single head. This technique is also inapplicable to opposed two headed systems, particularly in light of the of the line source's height, the need to provide effective shielding between the line source and the second detector while reducing the effective height of the source assembly, the limitations imposed by the frame, and the inability to adjust the relative distances between the transmission source, the object being imaged, and the detector.

Scanning line sources have also been used in two head right angle systems wherein the detectors are mounted at a 90° angle to each other. In such a system, however, close body orbits are problematic because one head can get in the way of the other and the patient is not centered in the field of view. Accordingly, it is desirable to apply a line source in a system having opposed detectors.

One technique for transmission imaging in an opposed detector system is to mount the line source at the side of one of the opposed detectors. A significant drawback to this approach is that the collimator of the opposed detector must be modified to allow detection of the transmitted radiation, which can increase patient to detector distance and adversely affect resolution and image quality. Such a modification has a deleterious effect on the detector's field of view.

Yet another drawback to the many prior art line source techniques is that radiation emitted by the line source but not attenuated by the subject reaches the detector without substantial attenuation. This "shine by" radiation results in extraneous detector counts and can cause saturation of the detector, leading to inaccuracies in the image data. One attempt to reduce the "shine by" radiation is disclosed in U.S. Pat. No. 5,576,545 ('545) assigned to Siemens Medical Systems, Inc. The '545 patent discloses the use of five mechanically rotatable shutters which can each be selectively positioned to attenuate radiation emitted by the line source. Accordingly the '545 patent discloses attenuating a greater percentage of the radiation as the line source is moved past regions where radiation would have otherwise "shined by" an object being imaged. This reduces the possibility of saturating the detector. In the '545 patent, the amount of attenuation occurring at any given time is governed by the number of shutters positioned in front of the line source. By rotating more shutters in front of the line source, or in other words by varying the overall thickness of attenuating material which the radiation from the line source must pass, the amount of attenuation is varied. Unfortunately there are several drawbacks to the solution proposed in the '545 patent. One drawback is that the proposed solution requires many mechanical and electrical components to control the positioning of the shutters adding cost and complexity to the system. Further, the '545 solution only provides for attenuation of the line source radiation in a direction perpendicular to a longitudinal axis of the examination region thereby limiting its usefulness.

The present invention contemplates a new and improved scanning line source which is particularly suited to two headed gamma cameras and other gamma cameras having opposed detector heads. The present invention further contemplates a technique for shaping the intensity of the transmitted radiation so as to reduce the undesirable effects of shine by radiation. As described more fully below, present invention overcomes the above-referenced problems and others.

SUMMARY

A new and improved scanning line source method and apparatus for a SPECT or nuclear camera is provided. A gantry movably supports at least one detector head for movement around an examination region. The detector head receives radiation from the examination region and generates data indicative of the received radiation. A transmission radiation source is mounted across the examination region from the detector head. The transmission radiation source includes a filter for attenuating radiation from the transmission radiation source such that the radiation has a desired intensity profile which minimizes the effects of "shine by" radiation on the detector. The filter includes at least one layer of radiation attenuating material which is of uniform thickness but varies in shape to obtain the desired intensity profile.

According to one aspect, the invention comprises a means for varying an amount of attenuation of the transmission radiation, the means varying in shape in a plane substantially orthogonal to a direction the transmission radiation is emitted.

According to a more limited aspect of the present invention, the amount of attenuation of the transmission radiation is generally related to the attenuating characteristics of an object situated in the examination region such that the amount of attenuation of the transmission radiation is relatively lower in at least a region where the object does not substantially attenuate the transmission radiation.

According to yet another more limited aspect of the invention, the means is a filter situated in the plane, the filter having at least one layer of radiation attenuating material of uniform thickness and of varying width.

According to another aspect of the present invention, a transmission radiation source is movably coupled to detector of a gamma camera. A filter having at least one layer of radiation attenuating material is positioned between the transmission radiation source and a examination region. The filter includes at least one layer of radiation attenuating material having a width which varies in a direction parallel to the direction of motion of the transmission radiation source.

According to another aspect of the present invention, a method of diagnostic imaging is provided. The method includes the steps of detecting radiation emitted by an object in the examination region of a nuclear camera, scanning a radiation source across at least a portion of the examination region, the radiation source emitting transmission radiation, varying an amount of attenuation of the transmission radiation in a direction substantially parallel to a direction the transmission radiation source is scanned, detecting the transmission radiation, and reconstructing an image representation from the radiation emitted by the object and correcting the image representation in accordance with the transmission radiation.

One advantage of the present invention is that spurious transmission radiation counts in the detector behind the line source are reduced.

Another advantage of the present invention is that filters for attenuating radiation emitted from the line source which may otherwise saturate the detector is made of layers of radiation attenuating material which are easy to manufacture.

Yet another advantage of the present invention is that the filters for attenuating radiation emitted from the line source may be readily removed and replaced to ensure a proper attenuation profile is obtained with respect to the object being imaged without the need for complex and expensive electrical and mechanical connections.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION

Figure 1:
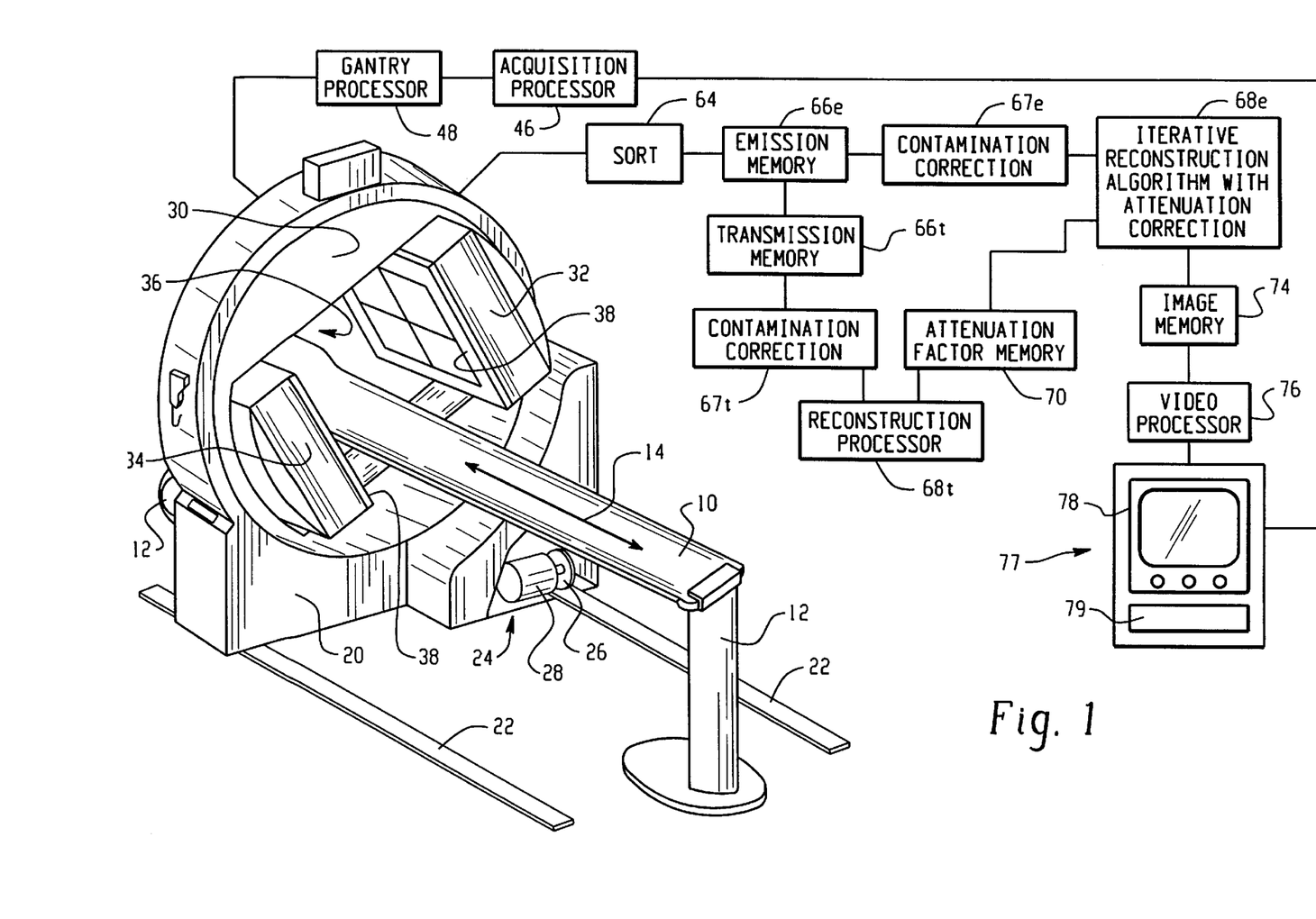
FIG. 1 is a perspective view of a gamma camera system in accordance with the present invention.

With reference to FIG. 1, a subject support or table 10 is mounted to stationary, vertical supports 12 at opposite ends. The subject table is selectively positionable up and down to center the subject in the center of a circle along a longitudinal axis 14.

An outer gantry structure 20 is movably mounted on tracks 22 which extend parallel to the longitudinal axis. This enables the outer gantry structure to be moved parallel to the longitudinal axis 14. An outer gantry structure moving means 24 is provided for selectively moving the outer gantry structure 20 along the rails 22 in a path parallel to the longitudinal axis. In the illustrated embodiment, the longitudinal moving means includes drive wheels 26 for supporting the outer gantry structure on the tracks. A motive power source, such as a motor 28, selectively drives one of the wheels which frictionally engages the track and drives the outer gantry structure and supported inner gantry structure and detector heads therealong. Alternately, the outer gantry can be stationary and the subject support configured to move the subject along the longitudinal axis.

An inner gantry structure 30 is rotatably mounted on the outer gantry structure 20. A first camera or detector head 32 is movably mounted to the inner gantry structure. A second detector head 34 is movably mounted to the inner gantry structure opposite to the first camera head. The detector heads are independently movable toward and away from each other. The inner gantry structure defines a central, subject receiving aperture 36 for receiving the subject table and permitting relative movement with respect to the patient, particularly along the longitudinal axis. The aperture 36 is enlarged to receive the detector heads in any of a variety of displacements from a central axis and angular orientations.

The detector heads have collimators 38 to restrict received radiation to radiation traveling generally perpendicular to the detector faces. The detector heads also include a scintillation crystal that emits a flash of light in response to incident radiation and an array of photomultiplier tubes which converts the light into electrical signals. A resolver circuit resolves the x, y-coordinates of each light flash and the energy of the incident radiation.

Figure 2:
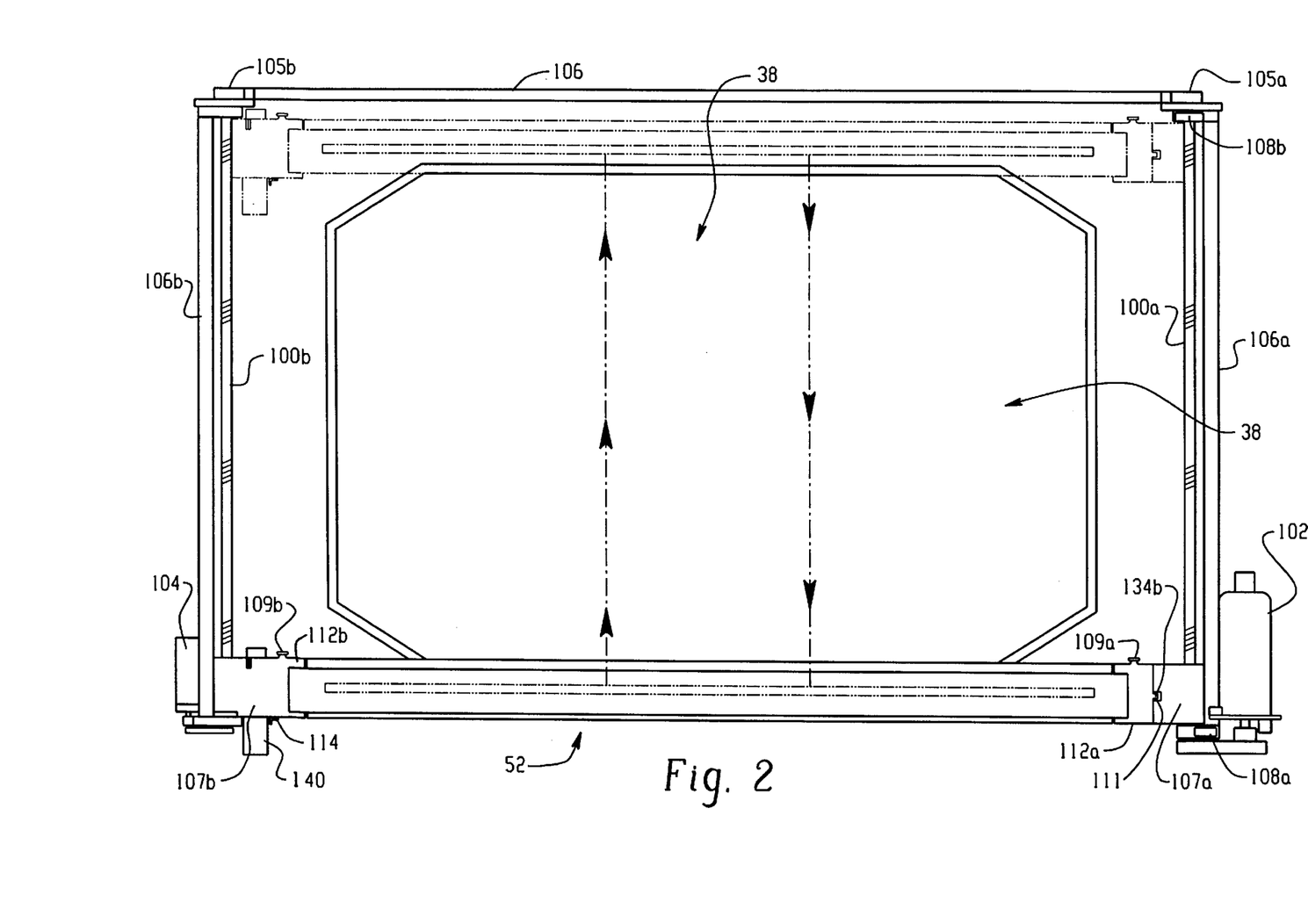
FIG. 2 is a front view of a detector and scanning line source according to the present invention.

With reference to FIG. 2, a transmission radiation source assembly 52 is disposed along the front surface of the collimator 38. Preferably, the radiation source assembly 52 is a line source extending across the collimator 38 in a direction substantially orthogonal to the longitudinal axis 14. The direction of motion is depicted by the arrows in FIG. 2; the source assembly 2 is shown in two representative positions. A drive mechanism moves the radiation source assembly 52 across the front of the collimator in the direction of the longitudinal axis 14. The transmission radiation source assembly 52 may also be mounted between the scintillation crystal and the collimator 38, or between the sections of a collimator having two or more sections. During operation, the collimator 38 and source assembly 52 are behind a cover and are thus hidden from view.

The source assembly 52 is driven by a DC motor 102 connected to acme screw drive assemblies 100a and 100b. The position and speed of the source assembly is sensed using an optical encoder integral to the DC motor 102 and a potentiometer 104. This information is used by the gantry processor 38 to provide closed loop control of the source assembly's position and speed. The gantry processor 38, power supplies, motor driver, and associated electronics are mounted in the rotating portion of the gantry 30. A cable carries signal and power to the drive components on the collimator 38.

The drive screw assemblies 100a and 100b are mounted on drive block support rails 104a and 104b. The support rails 104a and 104b are in turn mounted on the collimator 38. A timing belt transfers motive power from the drive screw assembly 100a to the drive screw assembly 100b via the pulleys 105a and 105b. Limit switches 108a and 108b provide a definitive indication of source assembly 52 position and establish end of travel limits. The potentiometer 104 provides an independent indication of drive screw 100b motion which is used to verify that drives screws 100a and 100b remain synchronized.

Figure 3:
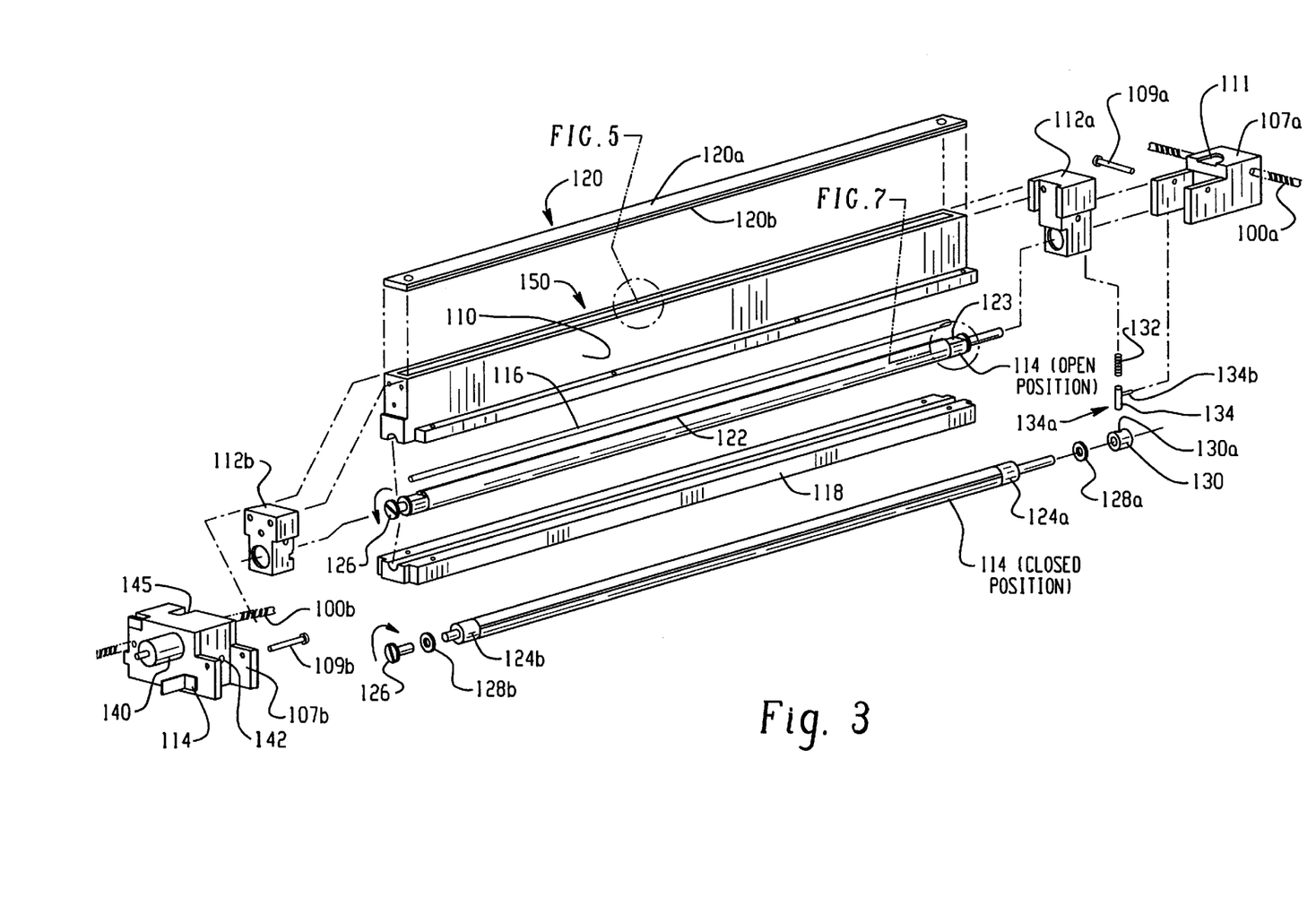
FIG. 3 is an exploded view of a scanning line source according to the present invention.

Drive blocks 107a and 107b engage the acme screws 100a and 100b. The radiation source assembly 52 is removably fastened to the drive blocks 107a and 107b using fasteners 109a and 109b such as pins, screws, clips, or the like which engage complementary apertures in the source assembly 52 and the drive blocks 107a and 107b. With reference to FIG. 3, bearing blocks 112a and 112b slidably engage within cavities defined by each of the drive blocks 107a and 107b. Hence, the source assembly 52 is inserted and removed from the drive blocks 107a and 107b in a direction perpendicular to the face of the collimator 38.

With reference to FIG. 3, the radiation source assembly 52 comprises a housing 110, source holder 114, radionuclide source 116, bottom cap 118, filter assembly 120, and bearing blocks 112a and 112b.

Figure 4:
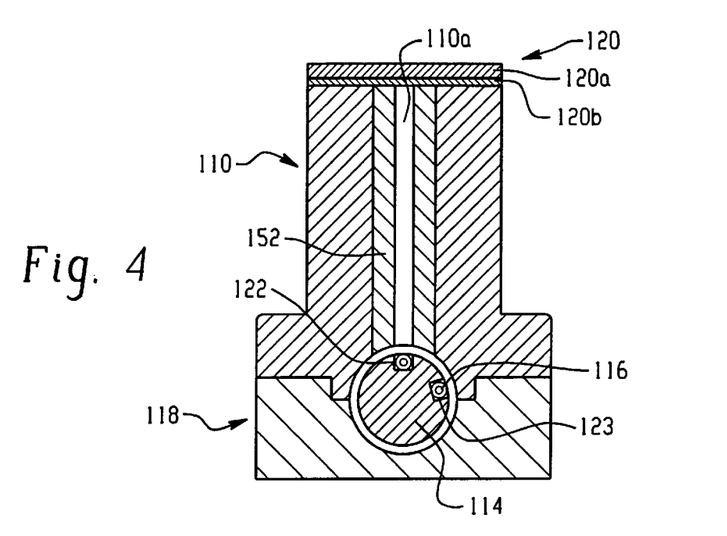
FIG. 4 is a side view depicting a cross section of a scanning line source according to the present invention.
Figure 5:
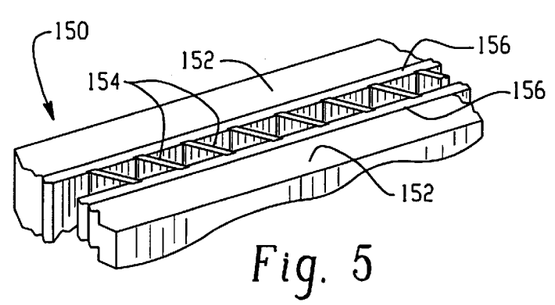
FIG. 5 depicts a top perspective view of a transmission collimator according to the present invention.

With reference again to FIGS. 4 and 5, the housing further includes a transmission radiation source collimator 150. The transmission collimator means 150 includes a pair of substantially parallel lead side walls 152. A plurality of thin septa 154 are mounted between the side walls 152. The septa 154 are constructed of a material which has good radiation stopping power and which, when struck by radiation, emits a gamma ray of relatively low energy, e.g., below 50 keV. Preferably, the septa 154 are constructed of tin or any alloy of tin and antimony. Tin emits gamma rays with a characteristic energy of about 30 keV. Other suitable materials for the septa include metals with an atomic number of about 30–70, particularly tin, antimony, zirconium, niobium, molybdenum germanium, yttrium, cerium, gadolinium, terbium, dysprosium, holmium, erbium, ruthenium, rhodium, palladium, silver, cadmium, indium, tellurium, cesium, barium, and alloys thereof. Of these, tin, antimony, molybdenum, zirconium, and cadmium are preferred for their more ready availability. The side walls of the collimator 152 could also be made of such materials. However, because many scans call for placing the detector heads as closely adjacent as possible, the transmission radiation source and collimator preferably have as narrow a profile as possible. To this end, the greater stopping power of lead, or other high atomic number material, which permits the radiation source assembly to be as small as possible is preferred. It will be noted that the surface area of the septa which are exposed to radiation from the line source is many times greater than the surface area of the side walls. Optionally, the side walls may be covered or plated on their exposed inside surfaces with tin or one of the other above-discussed metals to limit the emission of the 72 keV to 88 keV characteristic x-rays of lead.

The source holder 114 is preferably a cylindrical rod having a diameter of approximately 0.291 inches (7.4 mm). The source holder 114 contains a longitudinal groove 122 having a length, width, and depth sufficient to accommodate the radiation source. A depth of approximately 0.102 inches (2.6 mm) and a width of approximately 0.089 inches (2.3 mm) is suitable. The groove 122 has a generally rectangular cross section. The source holder 114 optionally but preferably comprises a further generally rectangular longitudinal groove 123 offset from the source holder groove 122 by about 75°. The rectangular groove 123 contains a radiation attenuating material such as tin, the depth and width of the groove and the attenuating material being selected to provide a desired radiation attenuation. The source holder 114 is comprised of a material which provides a desired degree of radiation attenuation, is relatively easy to machine, and exhibits sufficient structural rigidity. A suitable material is, for example, a high leaded tin bronze containing 81%–85% copper, 6.3%–7.5% tin, 6.0%–8.0% lead, 2.0%–4.0% zinc, 0.2% iron, 0.35% Sb, 1.0% Nickel, 0.8% sulfur, 0.15% P, 0.005% aluminum, and 0.005% silicon.

The diameter of the source holder 114 is reduced near the ends of the radionuclide source 116 to accommodate radionuclide source retaining clips 124a and 124b. The depth and width of the groove 122 are also increased near the ends of the radionuclide source 116 so that the radionuclide source 116 may be more readily gripped with a tool. To this end, the cross section of the groove 122 in this region is also generally trapezoidal with the larger dimension disposed at the outer edge of the source holder 114.

A slotted drive spindle 126 and ball bearing assembly 128a are affixed to the drive end of the source holder 114. A ball bearing assembly 128b and a locking disc 130 are affixed to the other end. The drive spindle 126, bearings 128a and 128b, and locking disc 130 define an axis of rotation about the center of the source holder 114.

The radionuclide source 116 is a cylindrical rod with a diameter slightly less than the width of the slot, for example, about 0.086 inches (2.2 mm). When inserted into the groove 122, the radionuclide source 116 is retained near to the periphery or outer edge of the source holder 114. Stated another way, the radionuclide source 116 is offset from the center of the source holder 114. The radionuclide source is also substantially offset from the source holder 114 axis of rotation. The radionuclide source 116 is, for example, a sealed steel tube containing a source such as Gd-153, Tc-99m, Co-57, or others.

The bottom cap 118 mates to the housing 110 and is removably fastened thereto using fasteners such as screws, clips, or the like. When mated, the bottom cap 118 and housing 110 define a cylindrical bore for receiving the source holder 114. The bottom cap 118 is a radiation attenuating material such as lead.

The filter 120 extends across an outlet aperture 120 of the transmission collimator 150 and is fastened thereto using fasteners such as screws. The filter 120 includes an inner layer 120b of a material which stops substantially all of the 72 keV to 88 keV energy x-rays from the lead in the side walls 152 of the transmission collimator, yet passes a substantial portion of the radiation from the transmission line source 116. The filter 120 further includes an outer layer 120a which stops substantially all of the lower energy radiation emitted by the inner layer 120b and by the septa 154. In the preferred embodiments in which the septa are tin or tin/antimony alloy, the inner layer 120b is also tin or tin/antimony and the outer layer 120a is aluminum. The aluminum not only absorbs gamma rays in the 30 keV range, but provides structural strength to the softer tin. Of course, the same alternate metals which can be used to construct the septa can also be used for the inner filter.

Optionally but preferably, a third filter layer is comprised of the same material as first layer is disposed at the output of the transmission collimator 150 upstream from the filter 120. The total thickness of the inner layer 120b and the third layer is adjusted to provide a desired attenuation.

Bearing block assemblies 112a and 112b are fastened to the housing 110 using fasteners such as screws, clips, or the like. The bearing blocks define apertures for receiving the ball bearing assemblies 128a and 128b. The bearing blocks 112a and 112b are preferably bronze.

Bearing block assembly 112a further comprises a spring 132 and a locking pin 134. The spring 132 urges the locking pin in the direction of the locking disc 130. A first protrusion or member 134a engages a radial aperture 130a in the locking disk 130. Hence, in a first position, the locking pin prevents the source holder 114 from rotating. A second protrusion or member 134b extends through a vertical slot (not shown) in the bearing block 112a. When the source assembly 52 is mounted on the collimator assembly 38, the second member 134b engages a groove 111 on the drive block 118, thereby urging the locking pin 134 against the spring. When in this second position, the first member 134a is no longer engaged in the locking disc 130. Hence, the locking pin 134 does not prevent rotation of the source holder 114.

With further reference to FIG. 3, the drive block assembly 107b further comprises an actuating solenoid 140, a mechanical linkage arrangement including a return spring (not shown), a rotate spindle 142, and a position sensor 144. The linkage includes a flag (145) which permits the position of the linkage and thus the source holder 114 to be ascertained visually and further permits manual positioning of the linkage.

The rotate spindle 142 includes a protrusion for engaging the slot on the drive spindle 126 when the source assembly 52 is installed on the collimator 38. When energized, the solenoid 140 engages the linkage arrangement, which converts the linear motion of the solenoid 140 into rotational motion and causes the rotate spindle 142 to rotate approximately 75°. The source holder 114 is thus rotated to a first or open position. When the solenoid is de-energized, the return spring causes the shutter rotate spindle 142 and hence the source holder 114 to rotate approximately 75° and return to the second or closed position. Position sensor 144 is used to confirm the actual position of the source holder 114.

Prior to installation of the source assembly 52 on the collimator 38, the locking pin 134 engages the locking disc 130. With reference to FIG. 3, the aperture 130a on the locking disc 130 and the groove 122 on the source holder are offset by about 75°. The radiation source 116 is thus locked in a position facing the side of the source housing 110. In this closed position, the radiation emitted by the source 116 is absorbed by the housing 110 and the source holder 114. The groove 123 is also generally aligned with the collimator slot 110a so that the radiation attenuating material contained in the groove 123 provides additional shielding against radiation emission through the collimator. The slot in the drive spindle 126 and the source holder groove 122 are likewise offset by about 75°. In the closed position, the slot on the shutter coupling 126 is therefore vertical. When the solenoid is de-energized, the protrusion in the shutter rotate spindle 142 is likewise vertical.

The source assembly 52 is installed on the collimator 38 by slidably engaging the bearing blocks 112a and 112b with the drive block 107a and 107b. The drive spindle 126 slot and the 25 rotate spindle 142 protrusion, both being vertical, likewise slidably engage. The first pin 134b on the locking pin 134 likes engages the groove 111 on the drive block 107a such that the second pin 134a on the locking pin 134 no longer engages the locking disc 130. The source holder 114 is thus free to rotate in response to rotation of the shutter rotate spindle 142. The fasteners 109a and 109b hold the source assembly 52 in place.

When energized, the solenoid 140 causes the rotate spindle 142, and hence the source holder 114 to rotate approximately 75° to the open position such that the radionuclide source 116 faces the transmission collimator 150. Hence, radiation emitted by the source 116 is emitted from the source assembly 52 through the examination region in the direction of the opposite detector. Because the rotate spindle 142 protrusion and the drive spindle 126 slot are approximately 75° from the vertical, the source assembly 52 cannot be removed from the drive blocks 107a and 107b while the source holder is in the open position.

When in the open position, the source holder 114 presents a substantial attenuation path between the radionuclide source 116 and the bottom cap 118. Hence, the source holder 114 presents a significantly greater attenuation path compared to source holders where the radionuclide source is located centrally. This increased attenuation path length provides increased design flexibility by allowing, for example, a reduction in the source assembly height, a reduction in source holder diameter, easier access to the radionuclide source, and construction of the source holder using a material having lesser radiation attenuating properties, while providing acceptable shielding between the radionuclide source and the detector to which the source is attached.

When the solenoid 140 is de-energized, the spring causes the shutter rotate spindle 142, and thus the source holder 114, to rotate approximately 75° back to the closed position. If desired, the source assembly 52 can again be removed from the collimator 38.

The radionuclide source 116 is replaced with the source assembly removed from the collimator 38. The bottom cap 118 is removed from the source housing 110 to permit access to the source holder 114. The second member 134b on the actuator pin 134 is depressed to permit rotation of the source holder 114, and the source holder 114 is rotated until the radionuclide source 116 is accessible. The second member 134b is then released such that first member 134b engages a second radial aperture (not shown) on the locking disc 130. The source holder 114 is thus locked in a third or source access position. The source retention clips 124a and 124b are rotated until slots disposed therein coincide with the radionuclide source, and the radionuclide source 116 is removed. The new radionuclide source 116 is installed and the retention clips 124a and 124b are rotated so that the radionuclide source 116 is again held in place. The first pin 134a is again depressed and the source holder 114 is manually rotated to the closed position. The first pin 134a is released such that the source holder 114 is locked in the closed position. The bottom cap 118 is reinstalled. The source assembly 52 can now be reinstalled.

Conventional gamma detector heads image radiation in two or more energy windows or ranges simultaneously. In a conventional dual energy gamma detector head, the signals are sorted based on amplitude. More specifically, energy windows or ranges are defined. Each window corresponds to a photopeak or energy spectrum of a radionuclide to be used in the examination. When using a radiation source 52, the injected or emission radionuclide has one preselected energy and the radiation source 52 or transmissive radiation has a second, different energy. In this manner, the detector heads 32 and 34 separate the transmission and emission radiation data by using the conventional energy separation circuitry used during dual injected radiopharmaceutical examinations. A position resolver (not shown) resolves the position on the crystal corresponding to scintillations or radiation events within each of the energy windows.

During a scanning operation, the collimator 38 of the preferred embodiment limits the emission and transmission radiation received by the detector face to radiation traveling generally perpendicular to the face. The non-perpendicular radiation is primarily absorbed by the collimator walls. Concurrently, the radiation source assembly 52 is moved across the face of the opposed detector by the drive mechanism. The transmission radiation from the radiation source 52 is also restricted by its associated collimator 150 such that only radiation that is substantially parallel to the collimator is allowed to pass through the collimator towards the subject. Thus, radiation which is not useful in creating a transmission image is prevented from being transmitted and absorbed by the subject. The transmission radiation from the radiation source 52 enters the subject and is attenuated by the subject and received by the opposite detector. The transmission radiation received by the opposite detector is used to create transmission projection data.

With reference again to FIG. 1, a reconstruction technique for emission and transmission data is provided. Of course, the reconstruction technique changes according to the types of radiation collected and the types of collimators used (i.e., fan, cone, parallel beam). Emission radiation from the subject is received by both detector heads 32 and 34 and emission projection data is generated. The emission data normally contains inaccuracies caused by varying absorption characteristics of the subject's anatomy. A sorter 64 sorts the emission projection data and transmission projection data on the basis of the relative energies. The data are stored in a projection view memory 66, more specifically in corresponding emission data memory 66e and transmission data memory 66t. Contamination correction 67e is applied to the emission data to correct for emission counts attributable to transmission radiation such as my be caused by scatter or varying composition of the transmission radionuclide source. Contamination correction 67t is similarly applied to the transmission data to correct for transmission counts attributable to emission radiation such as my be caused by scatter or varying composition of the emission radionuclide source. A reconstruction processor 68t reconstructs the transmission data into a transmission image representation or volume of attenuation factors stored in a memory 70.

Each voxel value stored in the memory 70 is indicative of attenuation of tissue in a corresponding location within the patient. An iterative reconstruction algorithm 68e reconstructs the emission data and also corrects the reconstructed image based on the attenuation factors contained in the attenuation correction factor memory 70. The reconstructed image representation is stored in a volumetric image memory 74. A video processor 76 withdraws selected portions of the data from the image memory 74 to generate corresponding human-readable displays on a video monitor 78. Typical displays include reprojections, selected slices or planes, surface renderings, and the like.

An operator control panel 77 includes a video monitor 78 for converting selected portions of the emission image representation into a human readable display. Optionally, transmission images might also be displayed. A keyboard 79 enables the operator to control the image reconstruction process, the selection of displayed data, the selection of preselected scanning procedures, and custom operation of the SPECT camera gantry. That is, the operator can control rotation of the rotatable gantry portion 30, movement of the detector heads 32, 34 radially toward and away from the examination region 36, positioning the patient couch 10, and the position of the line source assembly 52. The distance between each of the detectors 32 and 34 may also be independently adjusted. In particular, it is desirable that each detector head 32 be placed as close to the subject as possible.

It is also desirable to limit the radiation emitted by the source assembly 52 based on the dimensions and the attenuation characteristics of the object being imaged. Radiation from the transmission source assembly 52 traverses the examination region 36 and impinges on the opposing detector 32 or 34. Inasmuch as the object being imaged does not ordinarily fill the entirety of the imaging region 36, some of the transmitted radiation reaches the opposing detector without substantial attenuation. This unattenuated "shine by" radiation may be of sufficient intensity to saturate the detector, thereby distorting the images and attenuation measurements produced by the system. Accordingly, the intensity of the radiation transmitted by the source assembly is preferably varied in a manner generally inverse to the attenuating characteristics of the object being imaged such that detector counts attributable to the "shine by" radiation are reduced.

With reference to FIG. 6, the filter 120 comprises an aluminum substrate having a longitudinal channel 202. The length and width of the channel are sufficient to cover the outlet of the collimator 150. The depth of the channel is varied based on a desired attenuation profile. Stated conversely, the depth of the channel is varied so that the emitted transmission radiation has a desired intensity profile. The channel 202 contains a radiation attenuating material, for example a 90% tin, 10% antimony mixture. Of course, a shallower channel will provide relatively little attenuation, a deep channel will provide relatively more.

Figure 6A:
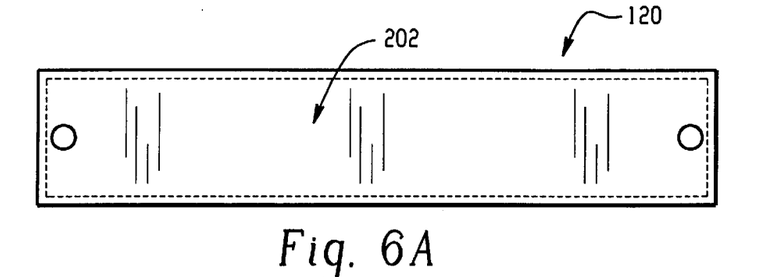
FIG. 6 depicts various beam shaping filters according to the present invention.
Figure 6B:
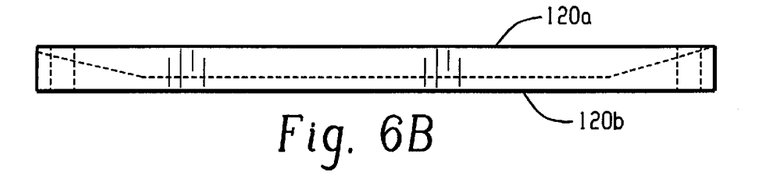
Figure 6C:
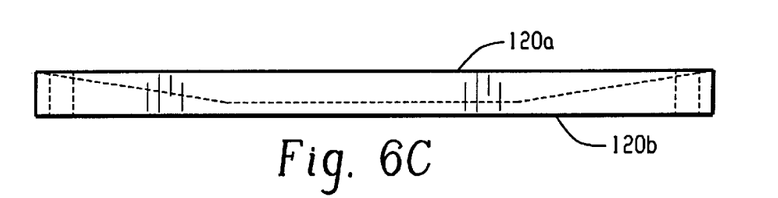

With reference to FIG. 6B, a filter adapted for imaging the torso attenuates the transmission radiation beam most strongly in the regions where the torso does not provide significant attenuation. In one embodiment, the channel has a constant, relatively shallow depth in the area of the torso. The depth of the channel increases beginning near the edge of the torso, increasing to a maximum near the edge of the filter. FIG. 6C depicts a filter adapted for imaging the head. Again, the thickness of the tin-antimony layer, and thus the amount of radiation attenuation, is generally inversely related to the attenuation provided by the object being imaged.

Figure 6D:
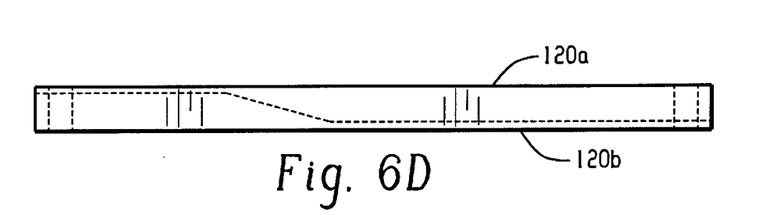

The filter has been described with respect to a system where the line source is disposed orthogonally to the longitudinal axis 14. The beam shaping filter is of course applicable to other configurations, including for example, systems in which the transmission source is disposed parallel to the longitudinal axis and systems having a fan transmission beam geometry. A head filter suitable for use in such a system is depicted in FIG. 6D.

The intensity of the transmitting radiation can be varied by other means. For example, it will be appreciated that the degree of attenuation can be altered by varying the composition of the radiation attenuating material. Alternatively, the activity of radionuclide source can be varied to produce a desired intensity profile.

As yet another alternative, the collimator slots may be blocked with shielding elements or pegs inserted at the outlet of the transmission source collimator 150. The pegs preferably comprise a radiation attenuation material such a tin or lead. The spacing of the pegs is varied such that the effective area of the collimator 150 output is varied according to the desired intensity profile. In the case of a torso filter, for example, the pegs are spaced increasingly closer together as one reaches the ends of the collimator. In this way, an intensity filter similar to those produced by the filters shown in FIGS. 6B–6F can be produced. Of course, other intensity profiles can readily be achieved.

Figure 6E:
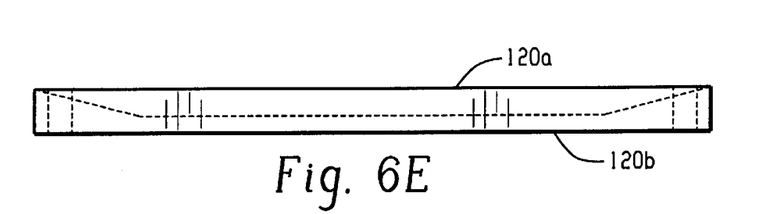
Figure 6F:
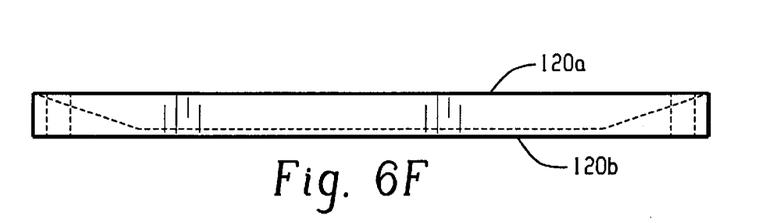
Figure 7:
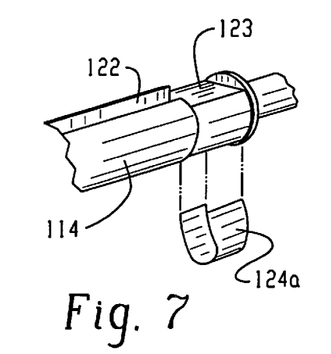
FIG. 7 is a detail view of radionuclide source retaining clips according to the present invention.

A family of filters having varying channel depths for each of the profiles is desirable. For example, the minimum thickness of the radiation absorbing material in one of the filters may be of an appropriate thickness to absorb about half of the transmission radiation from the radiation source. Another of the filters might have a thinner minimum thickness of the tin-antimony portion such that only about ¼ of the radiation is absorbed. Another one might only absorb ⅒ of the radiation, and so on. As the radiation source decays, the filters are replaced with filters which attenuate a progressively smaller percent of the radiation. In this manner, the output from the transmission line source assembly can be kept substantially constant over two or more half-lives of the radioisotope in the transmission radiation source. Examples of varying minimum thickness for a torso filter profile are depicted in FIGS. 6B, 6E, and 6F.

Each filter is preferably provided with distinctive colored markings to aid in identifying and selecting the appropriate filter. The selected filter is entered using operator interface 77 so that correct attenuation factors can be calculated based on the filter profile. Automatic coding of the filters, for example by electrical or optical coding, can be implemented so that appropriate attenuation factors are automatically determined.

In still another embodiment of the present invention, filter 120 may be constructed of at least one layer of radiation attenuating material which has a uniform thickness but varies in shape in a plane substantially orthogonal to a direction the radiation is emitted from the transmission source assembly 52 to obtain a desired radiation beam count profile. This embodiment is more clearly shown with reference to FIGS. 8 and 9. One reason for varying the shape of a layer of radiation attenuating material within such a plane as opposed to varying its thickness is to allow for easy stamping of such filters during manufacture. Thus, as discussed below, the present embodiment utilizes layers of material having uniform thickness but varying in shape to obtain desired radiation beam count profiles from the filter 120.

Figure 8:
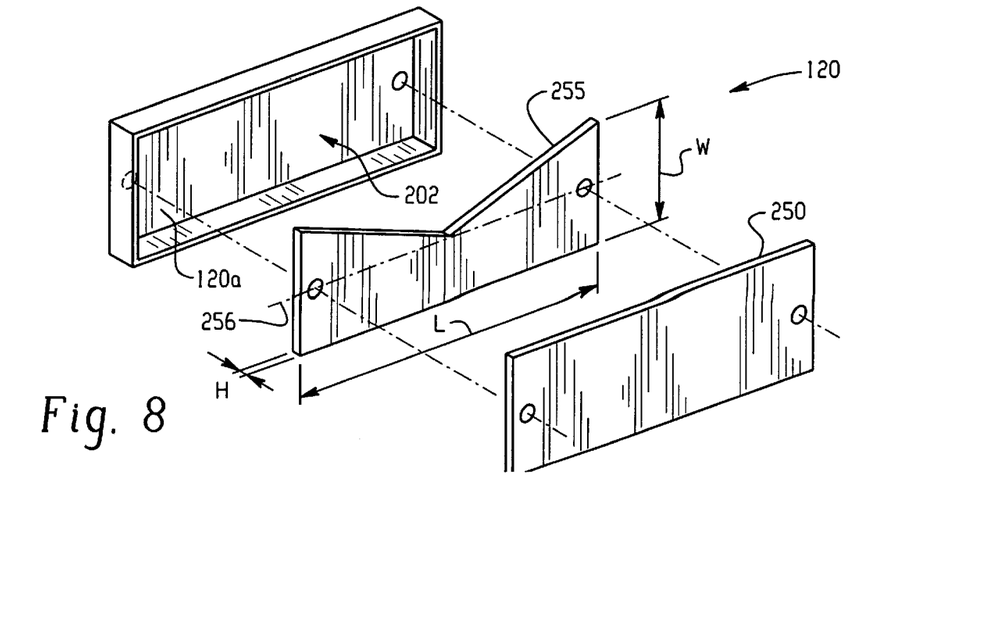
FIG. 8 is an exploded view of a beam shaping filter according to an alternative embodiment of the present invention.

As shown in FIG. 8, the layers of radiation attenuating materials of the present embodiment include a first filter layer 250 and an attenuation modifying filter layer 255 both disposed within the cavity 202 of the outer layer 120a. The first filter layer 250 is made of tin or a tin alloy such as tin-antimony and is uniform in both thickness and width. The attenuation modifying filter layer 255 is also made of tin or a tin alloy and in uniform in thickness. However, the width of the filter layer 255 varies along its length or "X" axis 256 so as to obtain a desired radiation beam count profile from the radiation which passes through the filter 120 as discussed in more detail below. In other words the width of the filter layer 255 varies in a direction parallel to a direction of motion M (see FIGS. 9A, 9B) of the transmission radiation source assembly 52 having filter 120. Thus, the intensity of the radiation passing thorough the filter 120 also varies in a direction parallel to a direction of motion M. The outer layer 120a is substantially the same as described above with respect to FIGS. 3–7. More specifically, the outer layer 120a is made of aluminum so as to attenuate low energy secondary radiation which may be transmitted from the tin filter layers 250, 255 while also is serving to add structurally rigidity to the filter 120. In the present embodiment the thickness of the filter layer 250 and outer layer 120a is 0.01 inches and the thickness of the filter layer 255 is 0.04 inches, however, it will be appreciated that the thickness of each filter layer 250, 255, 120a may be varied to obtain desired attenuation characteristics. Further, the radiation attenuating material of which filter layers 250, 255 and outer layer 120a are comprised may also be varied to obtain desired filtering characteristics or may be comprised of lead or other material which serves to completely absorb such radiation.

In the present embodiment, given that the shape and thickness of outer layer 120a and filter layer 250 are uniform, the radiation beam count profile is primarily governed by the shape of the filter layer 255. The radiation beam count profile refers to the number of photons per unit length times the beam width W which pass through the filter 120 each second. Thus, the units for the radiation beam count profile in the present embodiment is "photons/(unit length*beam width*sec)".

Referring now to FIG. 9, it is shown how modifying the shape, and in this case specifically the width, of filter layer 255 can produce a desired radiation beam count profile. More specifically, FIG. 9A shows a side profile of the filter 120 having three layers of radiation attenuating material with each layer being of uniform thickness. To obtain a desired radiation beam count profile as shown in FIGS. 9B'–9F', it is shown in FIGS. 9B–9F how the width of the filter layer 255 may be modified from the full width W of the filter 120. For example, referring to FIG. 9B, there are shown two segments $X_1$ and $X_2$ along the X axis 256 having a unit beam length of $X_L$ and a unit beam width of W. The number of photons which pass through each segment $X_1$ and $X_2$ can be measured. As the width of the filter layer 255 at point $X_1$ is narrower than the width at point $X_2$, the total number of photons which pass through the filter 120 is greater at segment $X_1$ than at segment $X_2$. Thus, the resulting radiation beam count profile across the full length L of the filter 120 of FIG. 9B (including points $X_1$, $X_2$) is shown in FIG. 9B'.

Figures 9A, 9B, 9C:
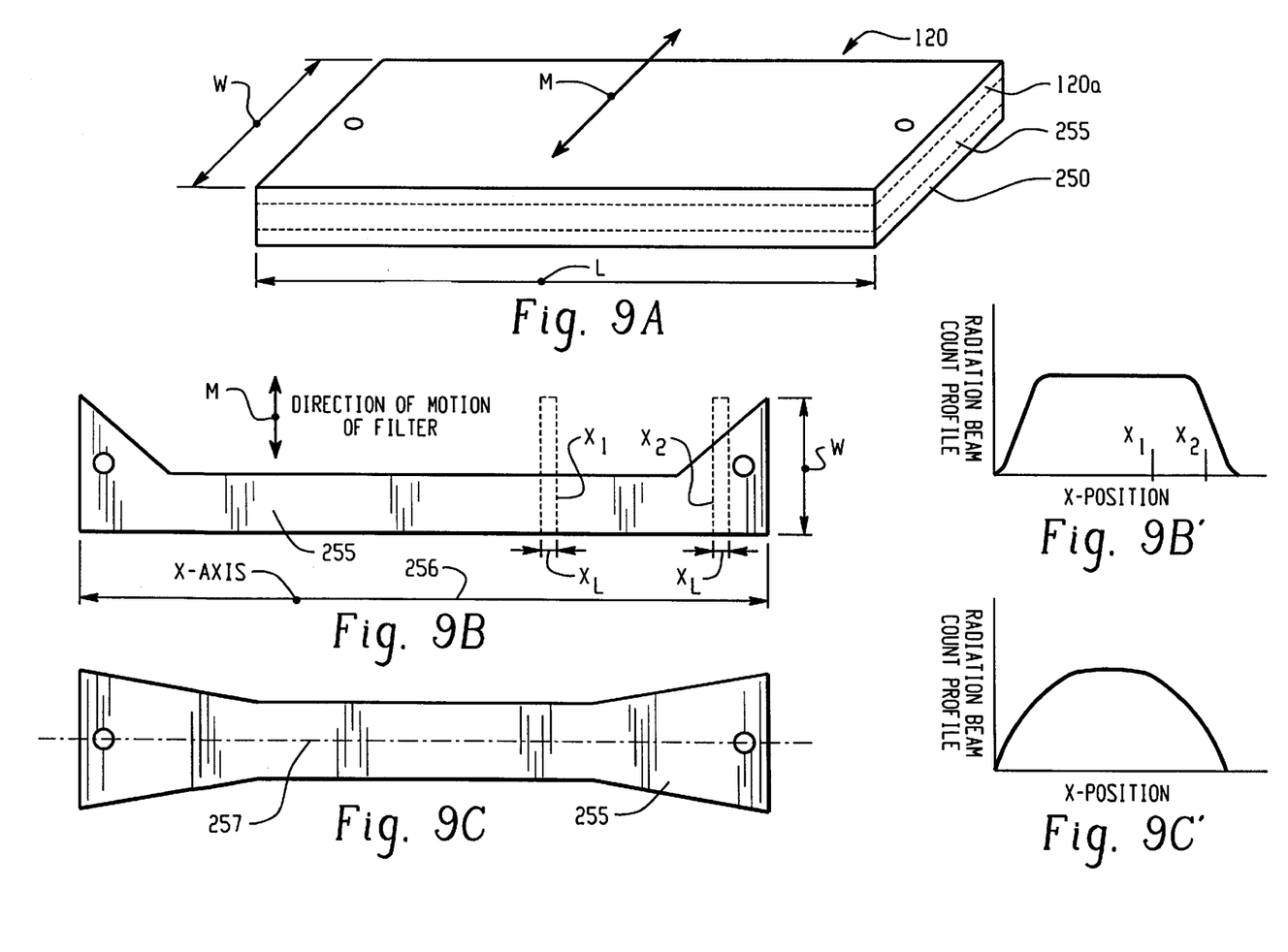
FIG. 9 depicts various beam shaping filters and associated intensity profiles in accordance with the alternative embodiment of the present invention.

In the present embodiment, the filter layer 255 of FIG. 9B is adapted for imaging a torso by way of attenuating more radiation per unit length times width W near ends of the filter layer 255 and attenuating a lesser amount of radiation between the ends. Comparatively, referring to FIG. 9C, the filter layer 255 is shaped for imaging of a head. The width of the filter layer 255 in FIG. 9C is shown to decrease symmetrically about the central axis 257 of the filter layer 255 to obtain the radiation beam count profile of FIG. 9C'. The filter layers 255 of FIG. 9D–9F similarly vary in width and are shaped to obtain radiation beam count profiles 9D'–9F' which may be useful in various circumstances similar to those described above with respect to FIGS. 6D–6F. Although only one exemplary shape of the filter layer 255 is shown in each example of FIG. 9, it will be appreciated that there are a multitude of ways of varying the shape to obtain a desired radiation beam count profiles which does not involve varying the thickness of any filter layer 250, 255, 120a.

Figure 9D:
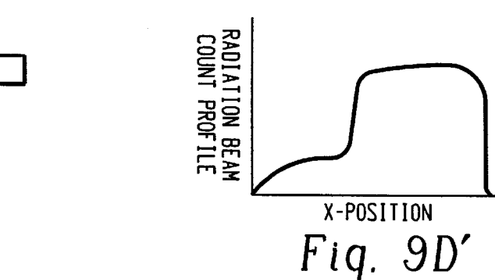
Figure 9E:
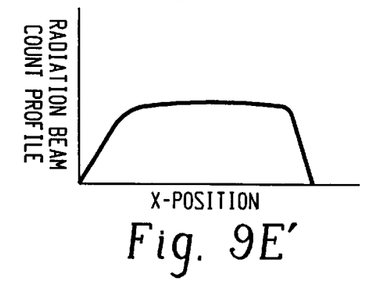
Figure 9F:
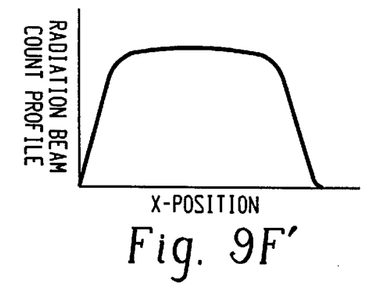
Figure 10A:
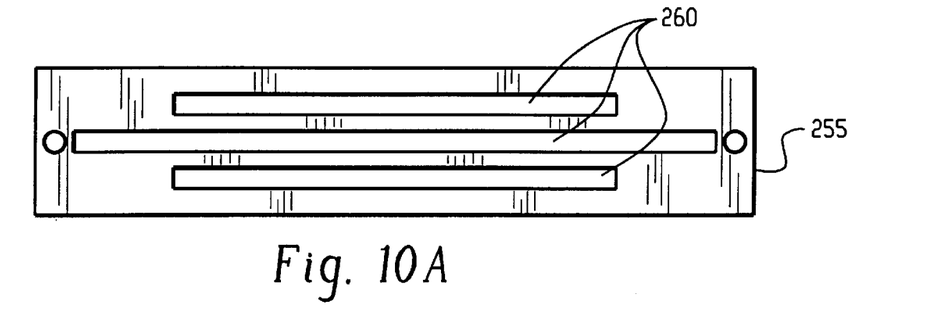
FIG. 10 depicts various additional beam shaping filters in accordance with alternative embodiments of the present invention.
Figure 10B:
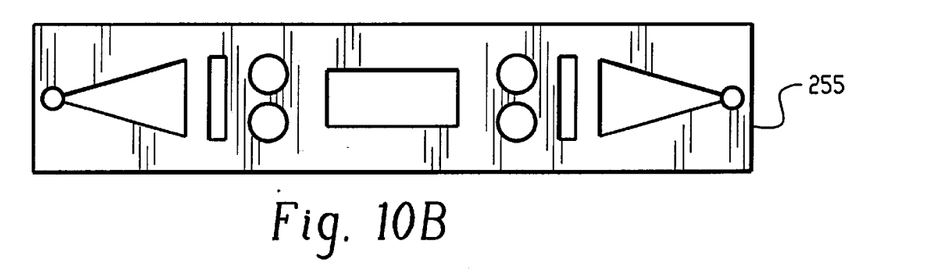
Figure 10C:
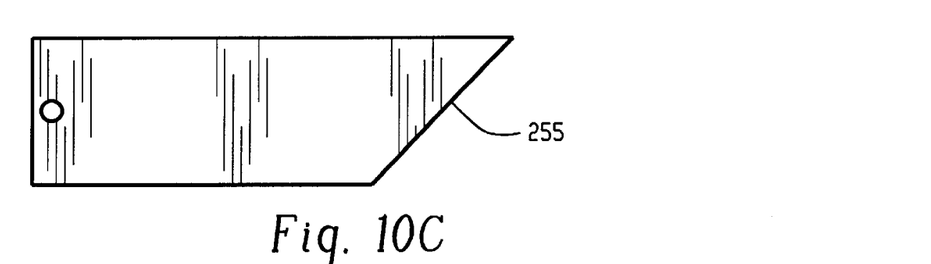
Figure 10D:
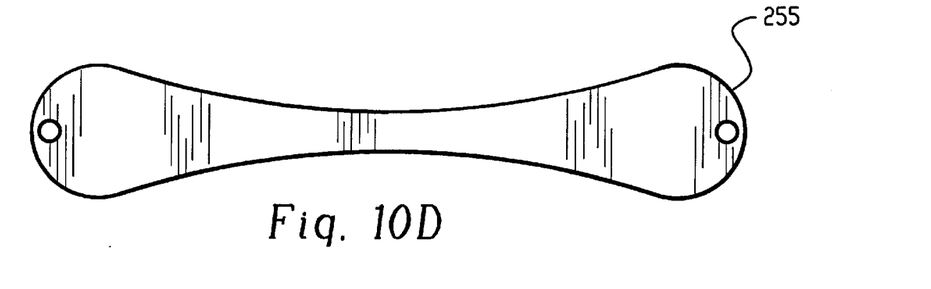

Referring now to FIG. 10, there is shown a variety of additional examples of the shapes in which the filter layer 255 may be varied to obtain a desired radiation beam count profile without varying the thickness of the filter layer 255. Generally, as discussed above, any change in surface area or shape of a filter layer 255 in a plane substantially orthogonal to a direction in which the radiation is traveling such that the number of photons per unit length times the beam width W is varied is sufficient to change the radiation beam count profile of a given filter 120. More specifically, it is shown in FIG. 10A that slits 260 may be cut into the filter layer 255 to obtain desired attenuation characteristics rather than changing the outer width. The slits may be of varying width, length, and number as needed. FIG. 10B shows a variety of different shaped cuts provided within the filter layer 255 which may also be useful to shape radiation beam count profile. FIG. 10C shows a filter layer 255 in which both the width and length is modified. The filter layer 255 of FIG. 10C could, for example, be used when a radiation beam count profile similar to FIG. 9D is desired. FIG. 10D shows a filter layer 255 in which the filter layer 255 includes curved edges along with a varying width W. The filter of FIG. 10D could be used to obtain a radiation beam count profile similar to that shown in FIG. 6C'. Thus, depending on the cost and ease of manufacturing and other factors, any of the above shapes and sizes of filter layers could be used. It will be appreciated that although the present embodiment has been described with respect to a filter 120 composed of three layers, the filter 120 could be composed of any number of suitable filter layers including only a single layer such as layer 255 if desired. Further, it will be appreciated that it would also be possible to have a filter layer which varied in both thickness and in width and/or length.

In operation, the filter 120 of the present embodiment reduces "shine by" radiation by virtue of reducing the number of photons per unit length times the beam width W which irradiates the detector head 32 (FIG. 1) in selected areas. For example, as the radiation source assembly 52 having filter 120 of FIG. 9B scans across the imaging region, a point on the detector head 32 in a line parallel to segment $X_1$ would receive more radiation over an given period of time than a point on the detector head 32 in a line parallel with segment $X_2$ (assuming uniform attenuation through the image region). This occurs since the width of filter layer 255 varies in a direction parallel to the motion M (FIG. 9B) of the radiation source assembly. Thus, in areas where the filter layer 255 is narrow in width (i.e. $X_1$), radiation having lower attenuation would reach the detector head 32 for a longer period of time than regions where the filter layer 255 were wider (i.e. $X_2$) in width as the radiation source assembly 52 is moved in direction M. If the filter layer 255 were made of lead, or other material capable of fully absorbing radiation, then the detector head 32 would receive no radiation in the regions which coincide with where the filter layer 255 spans the full width W of the filter 120 such as near the outer edges of the filter layer 255 shown in FIG. 9B. It will also be appreciated that if a fully absorbing filter layer 255 were used, than higher resolution images could be obtained by narrowing the width of the radiation beam in selected areas across the X axis 256.

Finally, it should be noted that more than one scanning line source may be installed on a given system. Each detector head is thus fitted with a line source as described above such that each detector head receives transmission radiation from an opposed transmission source.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A gamma camera system comprising:
   a gantry disposed about an examination region;
   at least a first detector head mounted to the gantry, the first detector head having a detector comprising a radiation sensitive face facing toward the examination region;
   a transmission radiation source for emitting transmission radiation in a direction which traverses the examination region and which is detectable by the first detector head; and
   means for varying an amount of attenuation of the transmission radiation, said means varying in shape in a plane substantially orthogonal to the direction the transmission radiation is emitted.

2. The system of claim 1 wherein the amount of attenuation of the transmission radiation is generally related to the attenuating characteristics of an object situated in the examination region such that the amount of attenuation of the transmission radiation is relatively higher in at least a region where the object does not substantially attenuate the transmission radiation.

3. The system of claim 1 wherein the means for varying comprises a filter disposed in the path of the transmission radiation.

4. The system of claim 3 wherein the filter comprises
   at least one layer of radiation attenuating material having a width which is varied according to a desired transmission radiation beam count profile.

5. The system of claim 4, wherein the at least one layer of radiation attenuating material is of uniform thickness.

6. The system of claim 4, wherein the filter further comprises a substrate defining a cavity and the at least one layer of radiation attenuating material is disposed in the cavity.

7. The system of claim 6 wherein the substrate comprises aluminum and the at least one layer of radiation attenuating material comprises at least one of tin and antimony.

8. The system of claim 3 wherein the filter comprises:
   a first layer of radiation attenuating material of uniform thickness;
   a second layer of radiation attenuating material of uniform thickness disposed on the first layer; and
   a third layer of radiation attenuating material of uniform thickness disposed on the second layer;

wherein a shape of the second layer is such that a desired radiation transmission beam profile is obtained.

9. A gamma camera system comprising:

a gantry disposed about an examination region;

a first detector head mounted to the gantry, the first detector head having a first detector comprising a first radiation sensitive face facing toward the examination region;

a second detector head mounted to the gantry opposite the first detector head, the second detector head having a second detector comprising a second radiation sensitive face facing toward the examination region;

a transmission radiation source movable across the second detector head and emitting transmission radiation which traverses the examination region and which is detectable by the first detector head; and a filter having at least one layer of radiation attenuating material disposed between the transmission radiation source and the examination region, a width of the layer varying in a direction parallel to the direction of motion.

10. The system of claim 9, wherein the filter attenuates the transmission radiation in a manner substantially inversely related to an amount attenuation occurring to the transmission radiation as it passes through the examination region.

11. The system of claim 10 wherein the at least one layer of the filter is of uniform thickness.

12. The system of claim 11, wherein the filter further comprises a substrate defining a cavity and the at least one layer of the filter is disposed in the cavity.

13. The system of claim 12 wherein the substrate comprises aluminum and the at least one layer of radiation attenuating material comprises at least one of tin and antimony.

14. The system of claim 9, wherein the direction of motion is substantially orthogonal to a longitudinal axis of the examination region.

15. A method of diagnostic imaging comprising the steps of:

detecting radiation emitted by an object in the examination region of a nuclear camera;

scanning a radiation source across at least a portion of the examination region, the radiation source emitting transmission radiation;

varying an intensity of the of radiation emitted by the radiation source in a direction substantially parallel to a direction the transmission radiation source is scanned, wherein a filter is disposed between the radiation source and the examination region for varying the amount of attenuation of the transmission radiation and the filter comprises at least one layer of radiation attenuation material varying in width;

detecting the transmission radiation;

reconstructing an image representation from the radiation emitted by the object; and correcting the image representation in a accordance with the transmission radiation.

16. The method of claim 15, wherein the at least one layer is of uniform thickness.

* * * * *